United States Patent [19]

Balsari et al.

[11] Patent Number: 5,286,851
[45] Date of Patent: Feb. 15, 1994

[54] MONOCLONAL ANTIBODIES TO ANTHRACYCLINES

[75] Inventors: Andrea Balsari; Maria I. Colnagh; Mario Ghione, all of Milan, Italy

[73] Assignee: Istituto Nazionale Per Lo Studio E La Cura Dei Tumori, Milan, Italy

[21] Appl. No.: 271,948

[22] Filed: Nov. 15, 1988

[30] Foreign Application Priority Data

Nov. 17, 1987 [IT] Italy .................. 22661 A/87

[51] Int. Cl.⁵ .............................. A61K 35/14
[52] U.S. Cl. ................ 530/388.9; 530/387.1; 530/388.1; 530/389.8; 530/391.1
[58] Field of Search ............... 935/90, 92, 103, 107, 935/110; 435/7

[56] References Cited

U.S. PATENT DOCUMENTS 4,517,289  5/1985  Milford et al. .................. 435/7

FOREIGN PATENT DOCUMENTS 0044441  1/1982  European Pat. Off. .

OTHER PUBLICATIONS

Balsari et al, Int. J. Cancer, 1988, 42 (5), 798–802, Monoclonal Antibodies Against Doxorubicin.
Kohler et al, Nature, 256; 496–497, 1975, Continuous Cultures of Fused Cells Secreting Antibody of Predefined Specificity.

*Primary Examiner*—Robert J. Hill, Jr.
*Assistant Examiner*—Laurie Scheiner
*Attorney, Agent, or Firm*—Walter H. Schneider

[57] ABSTRACT

Monoclonal antibodies able to selectively bind to doxorubicin and its analogues and derivatives are disclosed.

3 Claims, No Drawings

MONOCLONAL ANTIBODIES TO ANTHRACYCLINES

The present invention concerns hybridomas secreting monoclonal antibodies able to selectively bind to doxorubicin as well as to analogues and derivatives thereof.

The invention concerns also the monoclonal antibodies secreted by said hybridoxas able to selectively bind to doxorubicin.

A further object of the invention is provided by diagnostic and/or therapeutic applications of the above cited monoclonal antibodies.

The development of the somatic hybridization technique by G. Kohler e C. Milstein (Nature, 256; 495-497, 1975) allowed the possibility of obtaining unlimited amounts of monoclonal antibodies, i.e. of antibodies having a unique and defined specificity, recognizing a single antigenic determinant.

Said antibodies are secreted by hybrid cells, deriving from the fusion of immune lymphocytes against the desired antigen with a line of myeloma cells having specific characteristics, in order to impart immortality to the antibody producing lymphocyte cells.

In fact, the hybrid cells deriving from said fusion, exhibit both the properties of lymphocytes of producing antibodies of a given specificity and the immortal character of the parental tumor cell.

The hybrid cells are then cloned so as to obtain clones each deriving from a single cell, producing only one kind of antibody. The selected clone secreting the desired antibody may be kept viable indefinitely both by transplanting it in vivo in athymic mice and cultivating it in vitro.

Thus, a monospecific reagent, able to avoid cross-reactions typical of polyspecific sera which contain, in addition to the desired reagent, numerous antibody families with different specificities, will be always available in practically unlimited amounts.

There have been so far described monoclonal antibodies specific for different antigens of bacterial, viral, tumoral, humoral (horxones, proteins) origin, used for instance for diagnostic purpose in immunoenzymatic systems or the like, for preparative purpose, for instance for the purification of interferons, interleukins or even for therapeutic purposes, for instance in the extra-corporeal treatment of bone marrow to remove neoplastic cells or as carriers in vivo of cytotoxic agents. According to the latter aspect, the use of antitumor drugs conjugated to monoclonal antibodies directed to tumoral antigens, has been proposed.

Very few if any examples at all exist of monoclonal antibodies directed to low molecular weight compounds, poorly immunogenic, particularly of synthetic, semi-synthetic or fermentative (antibiotics) origin.

It has now been surprisingly found that it is possible, by suitably modifying the somatic hybridisation technique according to the invention, to obtain hybridomas secreting antibodies able to selectively bind to doxorubicin as well as to analogues and derivatives.

Doxorubicin, daunomycin and the semi-synthetic derivative epirubicin are drugs whose clinical effectiveness is widely known, belonging to the chemical class of anthracyclines; in addition to the above cited parent compounds, numerous derivatives have been synthetized aiming at increasing the therapeutic index.

The availability of monoclonal antibodies specific to antigenic determinants of said anthracyclines compounds allow different analytic-diagnostic and/or therapeutic applications.

The antibodies according to the invention have been obtained by immunizing BALB/c mice with doxorubicin or other anthracycline compound conjugated to a suitable carrier such as bovine serum albumine by means of carbodiimide (Hurxitz e coll., Cancer Res. 35; 1175, 1975).

The doxorubicin-carrier conjugate, after emulsion in complete Freund's adjuvant, has been administered by intramuscular, subcutaneous routes in subplantar pads of inbred BALB/c mice.

The immunization has been repeated at the $14^{th}$, $25^{th}$, $26^{th}$, $27^{th}$ days.

For the somatic hybridization of spleens withdrawn from immune mice three days after the last boosting, a cellular suspension has been prepared from which red blood cells were removed by treatment with 0.17 M $NH_4Cl$ for 10' at 4 C. $1.10^8$ splenic cells, after washing with Hank's saline balanced solution, were placed in a test-tube together with $2 \times 10^7$ cells of NS1 murine myeloma cells. This line of myeloma was cultured on RPMI 1640 medium containing 10% of fetal calf serum.

The NS1 and splenic cells mixture has been then treated according to the method described by Kohler e Milstein. After hybridization, the cells, re-suspended on RPMI with 20% fetal calf serum, were distributed in cell culture, 4 8 wells micro-plates (Costar, Cambridge, Mass. U.S.A.) in amount of 400,000 cell per well to which 0.3 ml of RPMI medium were added. On the subsequent day, 0.3 ml of HAT solution were added to each well. The cells were cultured for 15 days, changing the medium after 7 days.

The surnatants of each well were then tested for the production of antibodies by immunoenzymatic test (ELISA) on the doxorubicin-carrier conjugate and on the carrier alone. The hybridoxas contained in the wells whose surnatant reacted only on the doxorubicin-carrier surnatant were cloned by serial dilutions in 96 wells-plates in the presence of peritoneal cells of BALB/c mice as nutritive medium (Feeder-layer).

The RPMI medium added with HAT and fetal serum has been substituted with RPMI +HT medium (J.W. Lifflefield, Science 145: 709-710, 1964) and fetal serum for 5 days then with RPMI and fetal serum.

The products of the so cloned single hybridomas have been further characterized by radioisotopic binding test using as inhibitor doxorubicin itself and its analogues and derivatives, and some other chemotherapeutic agents.

In a series of monoclonal antibodies positive for doxorubicin, antibodies which are specifically directed to some antigenic determinants of the drug have been identified by the analysis of cross-reaction data with doxorubicin analogues, modified in one or more molecular sites.

Selected hyridomas were kept in vivo in peritoneal transplant in BALB/C mice pre-treated with 2,6,10,14-tetramethylpentadecane (pristane) in order to favour the ascitis formation. The monoclonal antibodies obtained according to the invention may be used in the monitoring of the chemotherapeutic treatment or as histopathologic reagents for the determination of the drug in different tissues, according to usual methods.

The monoclonal antibodies of the invention may also be used to modify the toxicity, either systemic or local, of the drug or to carry it on the target cells or to act as reagents in chemical or physical processes intended to obtain anthracyclines derivatives or complexes thereof.

We claim:

1. Monoclonal antibodies able to selectively bind to anthracycline compounds.

2. Monoclonal antibodies according to claim 1 directed against doxorubicin.

3. Hydridomas secreting monoclonal antibodies of claim 1.

* * * * *